United States Patent [19]

Gosling et al.

[11] Patent Number: 5,258,563
[45] Date of Patent: Nov. 2, 1993

[54] PROCESS FOR THE PRODUCTION OF BENZENE FROM LIGHT HYDROCARBONS

[75] Inventors: Christopher D. Gosling, Roselle; David A. Hamm, Hinsdale, both of Ill.

[73] Assignee: UOP, Des Plaines, Ill.

[21] Appl. No.: 897,133

[22] Filed: Jun. 11, 1992

[51] Int. Cl.⁵ .............................. C07C 1/00
[52] U.S. Cl. ......................... 585/322; 585/319; 585/804; 585/805; 585/407; 585/412; 585/413; 585/415
[58] Field of Search .............. 585/319, 322, 804, 805, 585/407, 412, 413, 415

[56] References Cited

U.S. PATENT DOCUMENTS

| | | | |
|---|---|---|---|
| 4,110,081 | 8/1978 | Millar et al. | 23/288 |
| 4,167,533 | 9/1979 | Raymond | 585/319 |
| 4,215,231 | 7/1980 | Raymond | 585/319 |
| 4,403,909 | 9/1983 | Greenwood | 414/786 |
| 4,642,402 | 2/1987 | Jensen | 585/411 |
| 4,654,455 | 3/1987 | Chao | 585/415 |
| 4,746,763 | 5/1988 | Kocal | 585/417 |
| 4,788,366 | 11/1988 | Harandi et al. | 585/415 |
| 4,806,700 | 2/1989 | Martindale | 585/322 |
| 4,936,976 | 6/1970 | Harandi et al. | 585/413 |
| 5,004,852 | 4/1991 | Harandi | 585/415 |

Primary Examiner—Patrick P. Garvin
Assistant Examiner—E. D. Irzinski
Attorney, Agent, or Firm—Thomas K. McBride; Eugene I. Snyder; Frank S. Molinaro

[57] ABSTRACT

A process is disclosed for the conversion of light aliphatic hydrocarbons such as propane into aromatic hydrocarbons and especially high purity benzene. The feed hydrocarbon is converted to aromatic hydrocarbons in a dehydrocyclodimerization zone. The product stream from the dehydrocyclodimerization zone which contains benzene, toluene, xylenes and $C_6$-$C_{10}$ non-aromatics are separated into an overhead stream which contains the non-aromatic hydrocarbons and a small fraction of the benzene and a bottoms stream which contains the remainder of the benzene and other aromatic components. The overhead stream is then flowed to a conversion zone where the $C_6$-$C_7$ non-aromatic hydrocarbons are cracked and the benzene is combined with the bottoms stream and further separated to give a high purity benzene product stream and a toluene, xylenes and $C_9+$ product stream. The toluene, xylenes and $C_9+$ product stream may further be separated into a toluene and xylenes product and a $C_9+$ product stream.

8 Claims, 1 Drawing Sheet

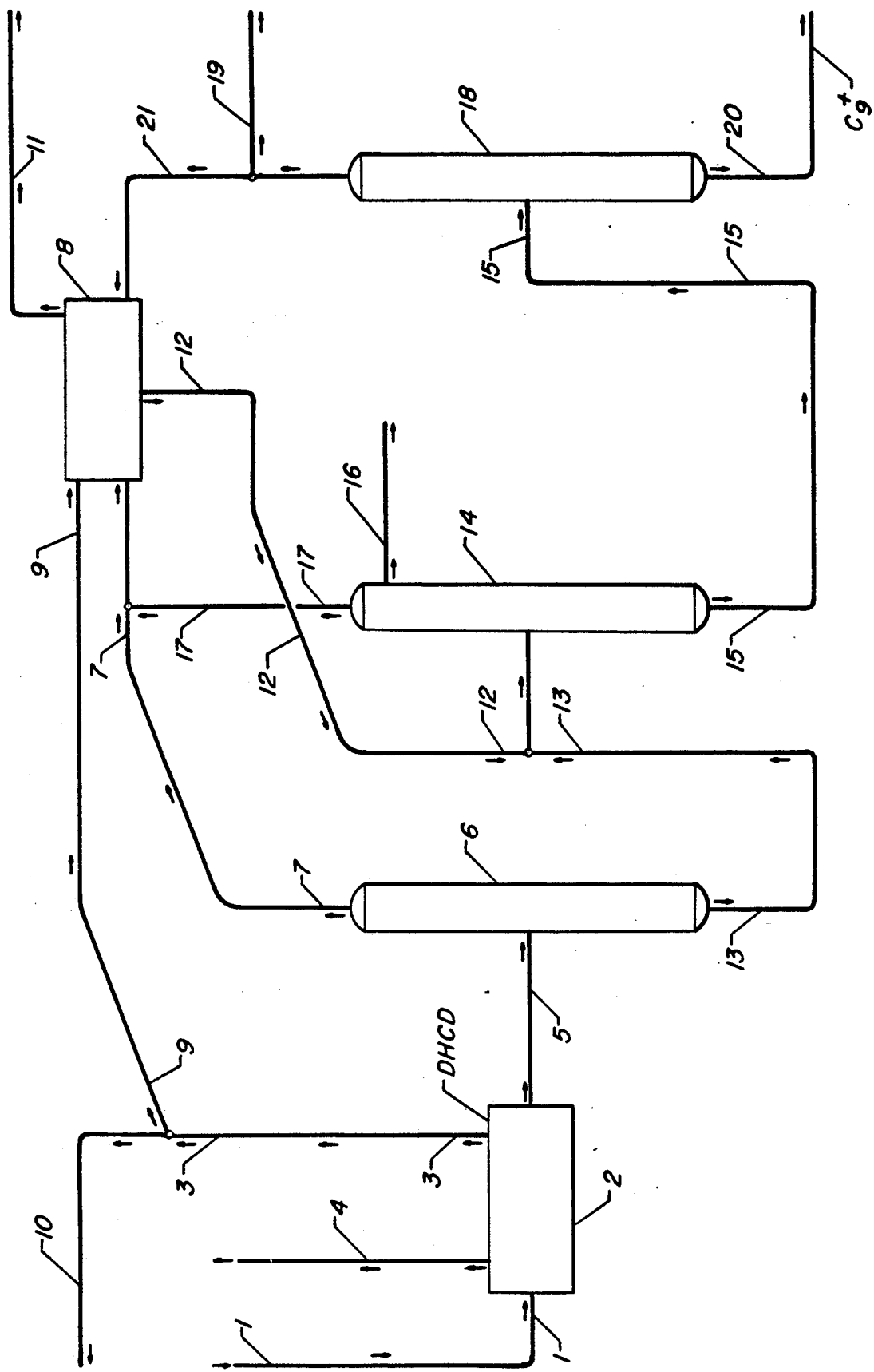

PROCESS FOR THE PRODUCTION OF BENZENE FROM LIGHT HYDROCARBONS

FIELD OF THE INVENTION

This invention generally relates to a hydrocarbon conversion process. Specifically, the process involves converting light aliphatic hydrocarbons such as propane to aromatic hydrocarbons and $C_6$-$C_{10}$ non-aromatic hydrocarbons. This product stream is further processed to separate most of the $C_6$-$C_7$ non-aromatic hydrocarbons with a small amount of benzene from the remainder of the aromatic hydrocarbons. The $C_6$-$C_7$ non-aromatic-rich process stream is flowed through a conversion zone where the non-aromatic hydrocarbons are converted to light hydrocarbons such as methane and ethane to provide a high purity benzene stream. This high purity benzene stream is mixed with the aromatic hydrocarbon stream and further processed to give a high purity benzene product stream.

BACKGROUND OF THE INVENTION

Dehydrocyclodimerization is a process in which aliphatic hydrocarbons containing from 2 to 6 carbon atoms per molecule are reacted over a catalyst to produce a high yield of aromatics and hydrogen along with a $C_6+$ non-aromatic byproduct. This process is well known and is described in detail in U.S. Pat. Nos. 4,654,455 and 4,746,763 which are incorporated by reference. Typically, the dehydrocyclodimerization reaction is carried out at temperatures in excess of 500° C., using dual functional catalysts containing acidic and dehydrogenation components. The acidic function is usually provided by a zeolite which promotes the oligomerization and aromatization reactions, while a non-noble metal component promotes the dehydrogenation function.

Since the product stream from the dehydrocyclodimerization process contains a mixture of compounds, it must undergo several separation steps in order to obtain usable products. An initial fractionation will separate any unreacted feedstream from a $C_6+$ product stream. The unreacted feedstream is recycled to the dehydrocyclodimerization zone while the product stream is fed to a second fractionation column to separate the product mixture into benzene, toluene, xylenes and heavier aromatics. Two references present schemes for optimizing the yield of aromatics from a dehydrocyclodimerization process. The first of these is U.S. Pat. No. 4,642,402 which discloses that the product stream from a dehydrocyclodimerization process is first processed to give a light gas stream which is recycled to the dehydrocyclodimerization zone and a liquid phase product stream which is flowed to a first fractionation column to remove $C_3$-$C_5$ hydrocarbons and provide a bottoms fraction which is high in benzene, toluene and xylenes. This bottoms fraction is now flowed through another fractionator which separates the benzene from the toluene and higher aromatics. A portion of the benzene is recycled to the dehydrocyclodimerization reaction zone to increase the yield of alkyl aromatics while the toluene and higher aromatic stream is further fractionated to give a toluene stream and a $C_8+$ aromatic stream.

U.S. Pat. No. 4,806,700 also discloses a process scheme for enhancing the purity of the aromatics which uses a hydrodealkylation zone. This reference discloses that the product stream from the dehydrocyclodimerization zone is flowed to a fractionator which separates a benzene stream from a bottoms stream which contains toluene and higher aromatics. The bottoms stream is flowed to a hydrodealkylation zone to dealkylate the alkyl chains on the aromatics and provide a benzene product as well as a $C_1$-$C_2$ light hydrocarbon stream which is vented. The benzene-containing product stream from the hydrodealkylation zone is further treated through a fractionation column to separate the benzene from the heavier aromatics.

Applicants have found that the benzene product from a dehydrocyclodimerization unit contains excessive amounts of non-aromatic $C_6$ and $C_7$ hydrocarbons which make it unsuitable for use in some petrochemical processes such as styrene or cyclohexane production. Neither of the process schemes described in the '402 or '700 references are suitable to provide a high purity benzene product since the '402 reference is aimed at providing a higher yield of toluene, while the '700 reference tries to increase the benzene yield by dealkylating alkyl aromatic compounds. Recognizing this need in the art, applicants have developed a process to give a benzene product that has a freezing point greater than or equal to 5.45° C. making it suitable for use in styrene or cyclohexane production.

Applicants take the product stream from the dehydrocyclodimerization zone and flow it to a fractionation zone which is operated at conditions such that the majority of the $C_6$ and $C_7$ non-aromatic hydrocarbons along with a portion of the benzene product is removed via an overhead stream. The bottoms product stream from this fractionation zone will contain benzene, toluene and xylenes. The overhead process stream from this first fractionation zone is flowed to a conversion zone, along with a hydrogen-rich gas, where the non-aromatic hydrocarbons are converted to light ($C_1$-$C_2$) hydrocarbons and a benzene fraction. The benzene fraction is combined with the bottoms fraction from the first fractionation zone and flowed to a second fractionation zone while the light hydrocarbons are vented. In this second fractionation zone the benzene is separated from the toluene, xylenes and heavier aromatics which in turn can be separated from each other in a third fractionation zone. An overhead stream can also be taken from this second fractionation zone which will contain some $C_6$ and $C_7$ non-aromatics along with some benzene and the second overhead process stream can also be flowed to the conversion zone to convert the non-aromatic hydrocarbons to light hydrocarbons and benzene.

SUMMARY OF THE INVENTION

This invention relates to a dehydrocyclodimerization process which yields high purity benzene as well as toluene and xylenes. Accordingly, one embodiment of the invention is a process for the production of aromatic hydrocarbons comprising:

a) flowing a hydrocarbon feedstream containing $C_2$-$C_6$ aliphatic hydrocarbons into a dehydrocyclodimerization zone where said feedstream is contacted with a bed of solid catalyst at dehydrocyclodimerization conditions, thereby producing a first product stream comprising benzene, toluene, xylenes, and $C_6$-$C_{10}$ non-aromatics;

b) flowing the first product stream to a first fractionation zone operated at conditions effective to separate the first product stream into a first fractionation zone bottoms stream which contains benzene, toluene and xylenes and a first overhead process stream which contains benzene and non-aromatic $C_6$-$C_7$ hydrocarbons;

c) flowing the first overhead process stream and a hydrogen-rich gas stream into a conversion zone operated at conversion conditions where the $C_6$-$C_7$ non-aromatic hydrocarbons are converted to $C_1$-$C_2$ hydrocarbons, thereby providing a second product stream containing benzene and a fuel gas stream containing $C_1$-$C_2$ hydrocarbons;

d) combining the second product stream and the first fractionation bottoms stream to provide a mixed stream which is flowed to a second fractionation zone operated at conditions effective to separate the mixed stream into a second fractionation zone bottoms stream which contains toluene, xylenes and $C_9+$ hydrocarbons and a final product stream containing benzene.

Other objects and embodiments of this invention will become more apparent after the detailed description of the invention.

BRIEF DESCRIPTION OF THE DRAWINGS

The drawing is a simplified process flow diagram of an embodiment of the invention showing the production of high purity benzene from a $C_2$-$C_6$ feedstream using a conversion zone.

DETAILED DESCRIPTION OF THE INVENTION

As stated, this invention relates to an improved process for the preparation of aromatic compounds and especially high purity benzene from a $C_2$-$C_6$ hydrocarbon feedstream. The feedstream to a dehydrocyclodimerization process contains light aliphatic hydrocarbons having from 2 to 6 carbon atoms per molecule. The feedstream may contain a single compound or a mixture of two or more of these compounds. The preferred feed compounds are propane, propylene, the butanes and the butylenes with saturates being highly preferred. It is preferred that the concentration of $C_5$ and $C_6$ hydrocarbons in the feedstream to a dehydrocyclodimerization process be held to a practical level, preferably below 20 mole percent. The principal products of the process are $C_6+$ aromatic hydrocarbons. However, dehydrocyclodimerization processes are not 100% selective and some non-aromatic $C_6+$ hydrocarbons are produced even from saturate feeds. The majority of the $C_6+$ product hydrocarbons will be benzene, toluene and the various xylene isomers with a small amount of $C_9+$ aromatics. The presence of olefins and $C_5+$ components in the feedstream results in increased production of $C_6+$ long chain non-aromatic products.

Regardless of the composition of the feedstream, the feedstream is flowed into a dehydrocyclodimerization zone which converts a significant portion of the aliphatic feedstream into aromatic hydrocarbons. The configuration of the reaction zone and the composition of the catalyst employed in the reaction zone are not basic elements of the invention nor limiting characteristics of the invention. The term "reaction zone" is intended to indicate the totality of the equipment employed in the dehydrocyclodimerization conversion step wherein the feed hydrocarbons are passed through a reaction chamber, which may contain a catalyst and the resultant hydrocarbons and any hydrogen are subsequently subjected to a series of steps including partial condensation and vapor-liquid separation for the generation of a liquid phase product stream and preferably one or more vapor-phase streams. As used herein, the term "reaction zone" is also intended to include a product stripping column located immediately downstream of vapor-liquid separation devices employed within the reaction zone when the use of such a stripping column within the reaction zone is desired.

The function of these separatory systems within the reaction zone is primarily to recover hydrogen for removal from the reaction zone or internal circulation within the reaction zone and also for the removal of light by-products such as methane and ethane from the liquid phase products of the reaction zones. The dehydrocyclodimerization (DHCD) reaction zone may employ a stripping column to separate the light gases commonly referred to as fuel gas from the liquid phase products. Alternatively, only a bulk partial condensation and phase separation may be preferred depending on such factors as utility (electricity, steam) costs, product distribution, feedstock costs, product values, etc. An engineering analysis based upon these and other factors which vary between installations must be performed to determine an optimum separation and product recovery flowscheme. When a bulk separation is used, the vapor-phase portion of the reaction zone effluent of the dehydrocyclodimerization zone is preferably separated by passage into a cryogenic separation system to yield a hydrogen stream, light off gases and feed hydrocarbons for recycling to the reaction zone.

Reaction zones which are used to contact hydrocarbon streams with a catalyst bed are well known in the art and are briefly described here only to provide a background to the subject invention. Usually the reaction zone consists of a moving bed radial flow multistage reactor as described for example in U.S. Pat. Nos. 4,110,081 and 4,403,909 which are incorporated by reference. These patents also describe catalyst regeneration systems and various aspects of moving catalyst bed operations and equipment. A preferred moving bed reactor system employs a spherical catalyst having a diameter between about 0.4 millimeters and 3.2 millimeters. The catalyst preferably comprises a zeolitic material, a metallic component and a binder. As stated, U.S. Pat. Nos. 4,654,455 and 4,746,763 which are incorporated by reference, describe catalysts where the zeolitic component is a ZSM-5 zeolite, the metallic component is gallium metal and the binder is a phosphorus-containing alumina binder. Methods of preparing these catalysts are also provided in these patents.

The dehydrocyclodimerization conditions which are employed in the reaction zone will vary depending on such factors as feedstock composition and desired conversion. A desired range of conditions for the dehydrocyclodimerization of $C_2$-$C_6$ aliphatic hydrocarbons to aromatics include a temperature from about 350° C. to about 650° C., a pressure from about 100 kPa to about 2,020 kPa and a liquid hourly space velocity from about 0.2 to about 5 hrs$^{-1}$. The preferred process conditions are a temperature in the range from about 400 to about 550° C., a pressure in the range from about 200 to about 1,015 kPa and a liquid hourly space velocity of between 1.0 to 4.0 hrs$^{-1}$. It is understood that as the average carbon number of the feedstream increases, a temperature in the lower end of the temperature range is required for optimum performance and conversely as the average carbon number of the feed decreases, the higher the required temperature.

The instant process uses a conversion zone to eliminate the $C_6$-$C_7$ non-aromatic components that are present in the product stream. Within this conversion zone the C$_6$-C$_7$ non-aromatic components are cracked to methane and ethane. Additionally, components such as toluene and xylenes can be hydrodealkylated, i.e., have their alkyl side chains removed. Hydrogen is a component in the reaction in order to completely crack the non-aromatic components to saturated alkyl components, i.e., methane and ethane. The cracking and/or the dealkylation reaction can be carried out either thermally or catalytically. Catalysts for such a conversion are well known in the art. The operating conditions for a zone include a temperature of about 540° to about 820° C. at the inlet of the reaction vessel, a pressure of about 2,000 kPa to about 7,000 kPa and a liquid hourly space velocity in the range of about 0.5 to about 5.0 hrs$^{-1}$. The reaction vessel contains sufficient internal structure to promote plug flow of the reactants through a portion of the vessel.

The drawing illustrates one embodiment of the invention. Those skilled in the art will recognize that this process flow diagram has been simplified by the elimination of many pieces of process equipment including heat exchangers, process control systems, pumps, fractionation column overhead and reboiler systems, etc. which are not necessary to an understanding of the process. It may also be readily discerned that the process flow presented in the drawing may be modified in many aspects without departing from the basic overall concept of the invention. Referring now to the drawing, a feedstream of propane representing the numerous feedstream compositions which may be flowed into the process is directed into a dehydrocyclodimerization (DHCD) reaction zone 2 through line 1. As stated, within the DHCD reaction zone the feedstream is contacted with a catalyst under DHCD conditions effective to convert a significant portion of the propane to aromatic hydrocarbons. This reaction step also releases hydrogen which is separated and released through line 3. Light hydrocarbons produced as a byproduct of the DHCD reaction are removed from the reaction zone through line 4. The liquid C$_6$+ hydrocarbons (first product stream) are removed from the bottom of a stripping column present within the reaction zone and are flowed through line 5 into the first fractionation zone 6.

The first product stream entering the first fractionation zone is separated into a first overhead process stream (which consists of about 3 to about 10 volume percent of the total hydrocarbons) which contains about 30 to 60% of the C$_6$-C$_7$ non-aromatic hydrocarbons and a first fractionation zone bottoms stream which contains the remainder of the benzene, toluene, xylenes, and C$_8$-C$_{10}$ non-aromatic hydrocarbons. The first overhead process stream is flowed through line 7 into a conversion zone 8. Also flowed into the conversion zone is a stream of high purity hydrogen from line 9. This hydrogen is derived from the DHCD reaction zone off-gas stream of line 3, with the portion not required in the conversion zone being removed through line 10 as a hydrogen product stream.

Within the conversion reaction zone the hydrocarbons of line 7 and the hydrogen of line 9 are flowed through a thermal reaction zone where the C$_6$-C$_7$ non-aromatic hydrocarbons are cracked to relatively light hydrocarbons. The effluent of the thermal reactor is partially condensed and separated in a vapor separation zone, not shown, to yield an off-gas stream removed from the process through line 11. This produces a second product stream which contains benzene and from about 5 to about 100 ppm non-aromatic hydrocarbons which is removed from the conversion zone through line 12 and combined with the first fractionation zone bottoms stream which is flowed through line 13. The mixed stream is flowed through line 13 into a second fractionation zone 14 which is operated at conditions effective to separate the mixed stream into a bottoms process stream which contains toluene, xylenes, and C$_9$+ hydrocarbons and which is removed via line 15 and a high purity benzene stream which is collected as a final product stream via line 16. If the quality of the benzene being withdrawn through line 16 is not sufficiently high enough, the second fractionation zone may be operated in such a manner that a second overhead process stream which contains a small amount of benzene and C$_6$-C$_7$ non-aromatic hydrocarbons is separated and withdrawn via line 17 and is combined with line 7 which is flowed into the conversion zone where the C$_6$-C$_7$ non-aromatic hydrocarbons are cracked to light hydrocarbons and the benzene is recovered via line 12.

The bottoms stream from the second fractionation zone 14 can either be collected as is or it may be flowed into a third fractionation zone 18 which is operated at conditions effective to separate the second fractionation bottoms stream into a toluene and xylenes product stream which is removed via line 19 and a C$_9$+ product stream which is removed via line 20.

If it is desired to produce as much benzene as possible, then an optional step in the process is to take the toluene and xylenes product stream from the third fractionation zone and flow it to conversion zone 8 via line 21 where the toluene and xylenes are converted (by hydrodealkylation) to benzene and methane. The benzene is then recovered as before via line 12.

Those skilled in the art of petroleum and petrochemical process design can determine proper operating conditions, vessel designs, and operating procedures for the subject process through the use of standard process design techniques after having now been appraised of the overall flow of the process. These design techniques should include a recognition that it is undesirable to pass compounds which may tend to freeze or otherwise solidify into any low temperature portion of the process. For this reason, a drying zone may be provided. The function of this drying zone would be to prevent the passage of water into the low temperature equipment used to obtain a high purity hydrogen off gas stream. The drying zone is basically required to remove the small amount of water which may be dissolved within the feed stream to the process and/or any water which may be present on regenerated catalyst passed into the process or released from stripping steam used to seal catalyst passageways, etc.

The vapor-liquid separation zones employed within the process preferably comprise a suitable sized vertically oriented vessel having a demisting pad or other liquid entrainment removal means provided at the upper end. The fractionation zones employed in the process preferably contain trayed fractionation columns having sieve-type trays and being of relatively standard design. For instance, a properly designed column having 40 trays will function as the fractionation column 6. Suitable fractionation zones may be readily designed by those skilled in the art. The operating conditions required in the fractionation zones are dependent upon the compounds being separated and the desired separation.

We claim as our invention:

1. A process for the production of aromatic hydrocarbons comprising:
   a) contacting a hydrocarbon feedstream containing $C_2$-$C_6$ aliphatic hydrocarbons with a bed of solid catalyst at dehydrocyclodimerization conditions in a dehydrocyclodimerization zone, thereby producing a first product stream comprising the feed hydrocarbon, benzene, toluene, xylenes, and $C_6$-$C_{10}$ non-aromatics;
   b) flowing the first product stream to a first fractionation zone operated at conditions effective to separate the first product stream into a first fractionation zone bottoms stream which contains benzene, toluene and xylenes and a first overhead process stream which contains benzene and non-aromatic $C_6$-$C_7$ hydrocarbons;
   c) flowing the first overhead process stream and a hydrogen-rich gas stream into a conversion zone operated at conversion conditions where the $C_6$-$C_7$ non-aromatic hydrocarbons are converted to $C_1$-$C_2$ hydrocarbons, thereby providing a second product stream containing benzene and a fuel gas stream containing $C_1$-$C_2$ hydrocarbons;
   d) combining the second product stream and the first fractionation zone bottoms stream to provide a mixed stream which is flowed to a second fractionation zone operated at conditions effective to separate the mixed stream into a second fractionation zone bottoms stream which contains toluene, xylenes and $C_9+$ hydrocarbons and a final product stream containing benzene.

2. The process of claim 1 where a second overhead process stream containing benzene and $C_6$-$C_7$ non-aromatic hydrocarbons is obtained from the second fractionation zone and flowed into the conversion zone.

3. The process of claim 1 where the second fractionation zone bottoms stream containing toluene, xylenes and $C_9+$ hydrocarbons is flowed to a third fractionation zone operated at conditions effective to separate the second bottoms stream into a toluene and xylenes product stream and a $C_9+$ product stream.

4. The process of claim 3 where the toluene and xylenes product stream is flowed to the conversion zone where the toluene and xylenes are converted to benzene and methane.

5. The process of claim 1 where the conversion zone is operated without the use of any catalyst.

6. The process of claim 1 where the dehydrocyclodimerization conditions include a temperature of about 350° to about 650° C., a pressure of about 101 kPa to about 2,020 kPa and a space velocity of about 0.2 to about 5 $hr^{-1}$.

7. The process of claim 1 where the conversion conditions include a temperature of about 538° to about 816° C., a pressure of about 2,069 kPa to about 6,895 kPa and a space velocity of about 0.5 to 5.0 $hr^{-1}$.

8. The process of claim 1 where the final product stream contains benzene that has a freezing point of greater than or equal to 5.45° C.

* * * * *